United States Patent
Ichikawa et al.

(10) Patent No.: US 9,133,193 B2
(45) Date of Patent: Sep. 15, 2015

(54) ORGANIC SEMICONDUCTOR MATERIAL, ORGANIC SEMICONDUCTOR THIN FILM, AND ORGANIC THIN FILM TRANSISTOR

(75) Inventors: Musubu Ichikawa, Nagano (JP); Naoki Hirata, Tokyo (JP); Hisao Kono, Tokyo (JP); Naomi Oguma, Tokyo (JP)

(73) Assignees: DAINICHISEIKA COLOR & CHEMICALS MFG. CO., LTD., Tokyo (JP); SHINSHU UNIVERSITY, Nagano (JP)

( * ) Notice: Subject to any disclaimer, the term of this patent is extended or adjusted under 35 U.S.C. 154(b) by 187 days.

(21) Appl. No.: 13/502,262

(22) PCT Filed: Oct. 29, 2010

(86) PCT No.: PCT/JP2010/069279
§ 371 (c)(1),
(2), (4) Date: Apr. 16, 2012

(87) PCT Pub. No.: WO2011/052721
PCT Pub. Date: May 5, 2011

(65) Prior Publication Data
US 2012/0199824 A1    Aug. 9, 2012

(30) Foreign Application Priority Data
Oct. 29, 2009 (JP) .................. 2009-249141

(51) Int. Cl.
*H01L 51/30* (2006.01)
*C07D 471/06* (2006.01)
*H01L 51/00* (2006.01)
*H01L 51/05* (2006.01)

(52) U.S. Cl.
CPC .......... *C07D 471/06* (2013.01); *H01L 51/0053* (2013.01); *H01L 51/0545* (2013.01)

(58) Field of Classification Search
USPC ....................................................... 252/500
See application file for complete search history.

(56) References Cited

U.S. PATENT DOCUMENTS

| | | | |
|---|---|---|---|
| 4,156,757 A | 5/1979 | Graser et al. | |
| 7,198,977 B2 | 4/2007 | Shukla et al. | |
| 7,326,956 B2 | 2/2008 | Shukla et al. | |
| 2002/0164835 A1 | 11/2002 | Dimitrakopoulos et al. | |
| 2005/0075453 A1* | 4/2005 | Mathauer et al. | 524/801 |
| 2005/0156161 A1 | 7/2005 | Hanna et al. | |
| 2006/0134823 A1 | 6/2006 | Shukla et al. | |
| 2007/0144579 A1 | 6/2007 | Jung et al. | |
| 2008/0224147 A1* | 9/2008 | Nagata et al. | 257/72 |
| 2008/0241990 A1* | 10/2008 | Kim et al. | 438/99 |
| 2010/0193777 A1 | 8/2010 | Takahashi et al. | |
| 2011/0042651 A1 | 2/2011 | Koenemann et al. | |

FOREIGN PATENT DOCUMENTS

| | | |
|---|---|---|
| JP | 2002-502893 | 1/2002 |
| JP | 2008-524846 | 7/2008 |
| JP | 2008-524869 | 7/2008 |
| JP | 2009-81265 | 4/2009 |
| JP | 2009-88483 | 4/2009 |
| JP | 2009-532436 | 9/2009 |
| WO | WO 03/067667 | 8/2003 |

OTHER PUBLICATIONS

Reid J. Chesterfield et al.: "Organic Thin Film Transistors Based on N-Alkyl Perylene Diimides: Charge Transport Kinetics as a Function of Gate Voltage and Temperature"; J. Phys. Chem. B, 108(50), 19281 (2004)—12 pages.

Ichikawa et al.: "High mobility n-type thin-film transistors based on N, N'-ditridecyl perylene diimide with thermal treatments"; Appln. Phys. Lett., 89(11), 112108 (2006)—3 pages.

C.W. Struijk et al.: "Liquid Crystalline Perylene Diimides: Architecture and Charge Carrier Mobilities"; J. Am. Chem. Soc., 122, 11057 (2000)—10 pages.

Che et al.: "Enhancing One-Dimensional Charge Transport through Intermolecular π—Electron Delocalization: Conductivity Improvement for Organic Nanobelts"; Journal of the American Chemical Society, ACS Publications, vol. 129, No. 20, Jan. 1, 2007, pp. 6354-6355, XP008154038.

Gregg et al.: "Doping Molecular Semiconductors: n-Type Doping of a Liquid Crystal Perylene Diimide"; Journal of the American Chemical Society, vol. 123, No. 32, Jan. 1, 2001, pp. 7959-7960, XP008154037.

\* cited by examiner

*Primary Examiner* — Harold Pyon
*Assistant Examiner* — Katie L Hammer
(74) *Attorney, Agent, or Firm* — Hamre, Schuman, Meuller & Larson, P.C.

(57) ABSTRACT

Provided are an organic semiconductor material, organic semiconductor thin film and organic thin-film transistor, which contain a perylene tetracarboxylic diimide derivative represented by the following formula (1):

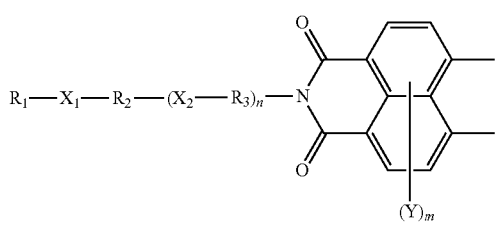

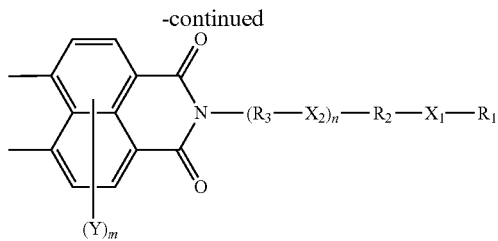

In the formula (1), $R_1$ means a linear or branched alkyl group having from 1 to 20 carbon atoms, $R_2$ means a linear or branched alkyl group having from 2 to 6 carbon atoms, $R_3$ means a linear or branched alkyl group having from 2 to 6 carbon atoms, $X_1$ and $X_2$ each mean a heteroatom selected from an oxygen atom, sulfur atom or selenium atom, Y means a halogen atom or cyano group, m stands for a number of from 0 to 4, and n stands for a number of from 0 to 2. Further, the alkyl groups represented by $R_1$ and $R_2$ may each be substituted with one or more fluorine atoms.

9 Claims, 4 Drawing Sheets

ORGANIC SEMICONDUCTOR MATERIAL, ORGANIC SEMICONDUCTOR THIN FILM, AND ORGANIC THIN FILM TRANSISTOR

TECHNICAL FIELD

This invention relates to an organic semiconductor material containing a 3,4:9,10-perylene tetracarboxylic diimide derivative, an organic semiconductor thin film comprised of the material, and an organic thin-film transistor making use of the organic semiconductor thin film. The 3,4:9,10-perylene tetracarboxylic diimide derivative has a cyclic conjugated skeleton structure formed of the perylene tetracarboxylic acid diimide ring, and also contains alkyl groups bonded to both of the nitrogen atoms of the cyclic conjugated skeleton structure, respectively. The alkyl groups each contain a divalent oxygen atom, selenium atom or sulfur atom.

BACKGROUND ART

The progress of a high-level information-oriented society in recent years is remarkable, and the development of digital technologies has led to the penetration of computers and communication technologies such as computer networks in everyday life. Keeping in step with this penetration, flat-screen TV sets and notebook-size personal computers have become increasingly popular, resulting in an increasing demand for displays such as liquid crystal displays, organic EL displays and electronic paper displays. Especially in recent years, there is an outstanding move toward larger displays of higher definition, and therefore, it is required to assemble an ever increasing large number of field-effect transistors corresponding to the number of pixels. In a liquid crystal display, the liquid crystal can be driven by providing the respective pixels with field-effect transistors as active elements and performing ON/OFF control of signals.

As field-effect transistors for use as active elements, thin-film transistors can be used. The performance of a thin-film transistor is determined by the kind and structure of its semiconductor material. In particular, the availability of high carrier mobility and high ON/OFF ratio makes it possible to obtain a large current. The availability of such a large current enables not only to drive an organic EL device or the like with a higher degree of accuracy but also to miniaturize the thin-film transistor and to provide an improved contrast.

For thin-film transistors useful as active elements, a silicon-based semiconductor material such as amorphous silicon or polysilicon can be used. A thin-film transistor is fabricated by forming such a silicon-based semiconductor material in a multilayered structure such that source, drain and gate electrodes are successively formed on a substrate.

For the fabrication of thin-film transistors making use of a silicon-based semiconductor material, however, large-scale and costly fabrication facilities are needed, and because of the use of photolithography, many process steps have to be gone through, resulting in an economical problem that the fabrication cost becomes higher. Furthermore, the fabrication requires high temperatures of from 300° C. to 500° C. or even higher, which lead not only to still higher fabrication cost but also to a technical problem that thin-film transistors can be hardly formed on plastic substrates or flexible plastic films.

On the other hand, organic thin-film transistors, which make use of organic semiconductor thin films comprised of an organic semiconductor material, are fabricated by various film-forming processes such as vapor deposition, printing and coating, and have the possibility of lower cost, larger area and lighter weight. Further, organic semiconductor thin films can be formed at a lower temperature compared with inorganic semiconductor layers, can realize cost reduction and can be formed on plastic substrates or flexible plastic films, and therefore, can be applied to lightweight and flexible, electronic devices or the like.

Many organic semiconductor materials have, therefore, been studied to date, and those making use of conjugated high-molecular compounds or low-molecular compounds as organic semiconductor thin films are known. Semiconductor materials include n-type semiconductor materials and p-type semiconductor materials, and there is a long-awaited desire for the development of n-type semiconductor materials and p-type semiconductor materials that exhibit still better transistor characteristics or the like. In an n-type semiconductor material, electrons move as main carriers to produce an electric current. In a p-type semiconductor material, on the other hand, holes move as main carriers to produce an electric current.

As organic semiconductor materials that exhibit high performance as organic thin-film transistors, pentacene materials and thiophene materials are known. These materials are semiconductor materials that exhibit p-type characteristics. However, reports on n-type organic semiconductor materials of high performance are limited. There is, accordingly, an outstanding desire for the development of n-type organic semiconductor materials of high performance. For further developments of organic electronics, lower power consumption, simpler circuits and the like are essential, and organic complementary MOS circuits which require both n-type and p-type organic semiconductor materials, such as complementary metal-oxide semiconductors (CMOS), are needed. There is, accordingly, an ever-increasing desire for the development of n-type organic semiconductor materials of high performance.

As n-type organic semiconductor materials, naphthaleneimide, naphthalenediimide, and derivatives thereof are known to date. However, none of these n-type organic semiconductor materials have been reported to have high performance as thin-film transistors. Further, Non-patent Document 1 describes the potential utility of low-molecular compounds, which have the perylene skeleton, in organic thin-film transistors capable of exhibiting high performance (Non-patent Document 1: 1.7 $cm^2/Vs$ electron mobility).

As to organic thin-film transistors making use of organic semiconductor films comprised of perylene tetracarboxylic acid derivatives and formed by vapor deposition, there are, for example, disclosures as will be described next. Patent Document 1 describes that a thin film transistor comprised of an organic semiconductor material layer, which contains a perylene tetracarboxylic diimide derivative having a carbocyclic or heterocyclic aromatic ring system substituted with fluorine-containing groups, has a mobility of from 0.05 to 0.2 $cm^2/Vs$ and an ON/OFF ratio of from $10^4$ to $10^5$ and exhibits stability in air and excellent reproducibility. Patent Document 2 describes that a thin film transistor comprised of an organic semiconductor material layer, which contains a perylene tetracarboxylic diimide derivative having substituted or unsubstituted phenylalkyl groups, has a mobility of from 0.04 to 0.7 $cm^2/Vs$ and an ON/OFF ratio of from $10^4$ to $10^5$ and exhibits stability in air and excellent reproducibility.

On the other hand, organic semiconductor thin films formed by the above-mentioned various film-forming processes generally have a polycrystalline structure formed of microcrystals aggregated together. Such organic semiconductor thin films each contain numerous grain boundaries (contacts between microcrystals), deficiencies and defects whichever material is used. These crystal grain boundaries, deficiencies and defects inhibit the transport of charges. These film-forming processes are, therefore, accompanied by a fabrication problem that they can hardly form an organic semiconductor thin film uniformly over a large area and are practically difficult to fabricate organic semiconductor devices having stable device performance. Organic semiconductor thin films formed especially by vapor deposition out of such various film-forming processes have a strong tendency to include crystal grain boundaries, deficiencies and defects.

To overcome such problems, the present inventors have already made a proposal as will be described below. Described specifically, the present inventors have solved the above-described problems by providing an organic thin-film transistor having an organic semiconductor thin film of N,N'-ditridecyl-3,4:9,10-perylene dicarboxylic acid imide, said organic semiconductor thin film having been formed by vapor deposition and having been subjected to heat treatment around a temperature at which N,N'-ditridecyl-3,4:9,10-perylene dicarboxylic acid imide presents a smectic liquid crystal phase (Non-patent Document 2:2.1 cm$^2$/Vs electron mobility). It is, therefore, possible to decrease the above-described crystal grain boundaries, deficiencies and defects and to form a uniform film by including the heat treatment and processing through the liquid crystal state.

PRIOR ART DOCUMENTS

Patent Documents

Patent Document 1: JP-A-2008-524846
Patent Document 2: JP-A-2008-524869

Non-Patent Documents

Non-patent Document 1: Reid J. Chesterfield, et al., J. Phys. Chem. B, 108(50), 19281 (2004)
Non-patent Document 2: Ichikawa et al., Appln. Phys. Lett., 89(11), 112108 (2006)

DISCLOSURE OF THE INVENTION

Problem to be Solved by the Invention

The above-described n-type organic semiconductor material, however, has low solubility in solvents so that it needs vapor deposition for its formation into a film and cannot use a printing process or a solution coating process such as spin coating. It is, therefore, the current situation that no organic semiconductor material has been found to have sufficient solubility in solvents to permit its formation into a film by a printing process or solution coating process and to facilitate the formation of an organic semiconductor thin film evenly over a large area although such formation has heretofore been difficult.

Moreover, an organic thin-film transistor to be fabricated by using the above-mentioned perylene tetracarboxylic diimide or derivative thereof as an organic semiconductor material requires the introduction of halogen atoms such as fluorine atoms for providing it with high transistor performance. This leads to a more complex or multi-stage process, and therefore, involves a problem from the standpoint of industrial fabrication that the organic semiconductor material becomes too costly to fabricate low price devices. There is, accordingly, an outstanding desire for the development of an organic semiconductor material, which is easy in production and is lower in cost, has higher performance as an organic semiconductor material, enables the formation of a film by a solution coating process such as spin coating or a printing process, facilitates the formation of an organic semiconductor thin film evenly over a large area, and permits the provision of an organic thin film layer or organic thin-film transistor having excel lent electron mobility and ON/OFF ratio.

An object of the present invention is, therefore, to provide an organic semiconductor material, which facilitates the formation of an organic semiconductor thin film evenly over a large area by any of various film-forming processes such as vapor deposition, printing and coating, and also enables to form an organic semiconductor thin film with a high electron mobility and a high ON/OFF ratio by a solution coating process using a solvent such as spin coating or by a printing process.

Other objects of the present invention are to provide an organic semiconductor thin film and organic thin-film transistor, which are excellent in characteristics and are produced and fabricated, respectively, by using the above-described organic semiconductor material. A still further object of the present invention is to provide an organic thin-film transistor comprised of a more uniform, organic semiconductor thin film by heat treatment.

Means for Solving the Problem

The above-described objects can be achieved by the present invention to be described hereinafter. Described specifically, the present invention provides an organic semiconductor material comprising a perylene tetracarboxylic diimide derivative represented by the following formula (1):

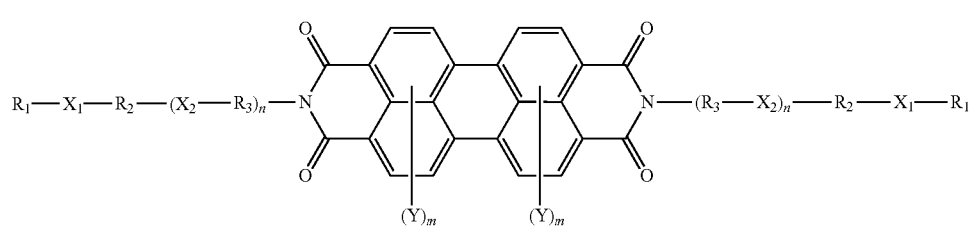

wherein $R_1$ means a linear or branched alkyl group having from 1 to 20 carbon atoms, $R_2$ means a linear or branched alkyl group having from 2 to 6 carbon atoms, $R_3$ means a linear or branched alkyl group having from 2 to 6 carbon atoms, $X_1$ and $X_2$ each mean a heteroatom selected from an oxygen atom, sulfur atom or selenium atom, Y means a halogen atom or cyano group, m stands for a number of from 0 to 4, n stands for a number of from 0 to 2, and the alkyl groups represented by $R_1$ and $R_2$ may each be substituted with one or more fluorine atoms.

In the present invention as described above, preferred is an organic semiconductor material of the formula (1), in which $R_1$ means a linear alkyl group having from 1 to 20 carbon atoms, $R_2$ means a linear alkyl group having from 2 to 6 carbon atoms, $R_3$ means a linear alkyl group having from 2 to 6 carbon atoms, $X_1$ and $X_2$ each mean an oxygen atom, Y means a halogen atom or cyano group, m stands for a number of from 0 to 4, and n stands for a number of from 0 to 2.

The present invention also provides an organic semiconductor material comprising, as a more specific one of the derivative represented by the formula (1), an N,N'-bis(3-($R_1$-oxy)-ethyl)-3,4:9,10-perylene tetracarboxylic diimide derivative represented by the following formula (2):

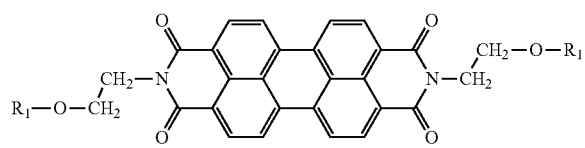

(2)

wherein $R_1$ means a linear alkyl group or branched alkyl group having from 1 to 20 carbon atoms.

The present invention also provides an organic semiconductor material comprising, as another specific one of the derivative represented by the formula (1), an N,N'-bis(3-($R_1$-oxy)-n-propyl)-3,4:9,10-perylene tetracarboxylic diimide derivative represented by the following formula (3):

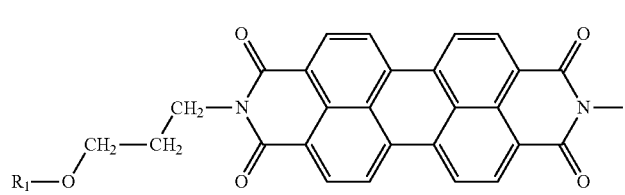

(3)

wherein $R_1$ means a linear alkyl group or branched alkyl group having from 1 to 20 carbon atoms.

The present invention also provides an organic semiconductor material comprising, as a further specific one of the derivative represented by the formula (3), N,N'-bis (3-(n-dodecyloxy)-n-propyl)-3,4:9,10-perylene tetracarboxylic diimide represented by the following formula (4):

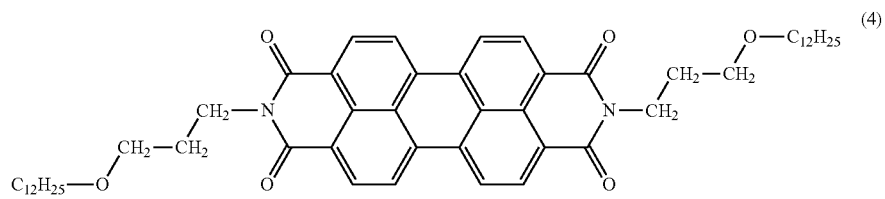

(4)

The present invention also provides an organic semiconductor thin film comprising the above-described organic semiconductor material according to the present invention; and an organic semiconductor thin film comprising the above-described organic semiconductor material according to the present invention and being capable of undergoing a phase transition into a liquid crystal state in a temperature range of from 100° C. to 250° C.

The present invention also provides an organic thin-film transistor formed on a substrate and having a gate electrode, gate insulating layer, organic semiconductor thin film, source electrode and drain electrode, wherein the organic semiconductor thin film comprises the above-described organic semiconductor thin film according to the present invention. The organic thin-film transistor may preferably have an electron mobility of from 0.01 to 5.0 cm$^2$/Vs.

The present invention also provides an organic thin-film transistor formed on a substrate and having a gate electrode, gate insulating layer, organic semiconductor thin film, source electrode and drain electrode, wherein the organic semiconductor thin film comprises the above-described organic semiconductor thin film according to the present invention, and the organic semiconductor thin film has been subjected to heat treatment at a temperature between 100° C. and 250° C. The organic thin-film transistor may preferably have an electron mobility of from 0.01 to 5.0 cm$^2$/Vs.

Advantageous Effects of the Invention

According to the present invention, there is provided an organic semiconductor material, which can form an organic semiconductor thin film with a high electron mobility and a high ON/OFF ratio even by a solution coating process using a solvent (solution) such as spin coating. According to the present invention, the use of the above-described organic semiconductor material makes it possible to provide an organic thin-film transistor which is excellent in characteristics and is of low price.

MODES FOR CARRYING OUT THE INVENTION

Figure 1:
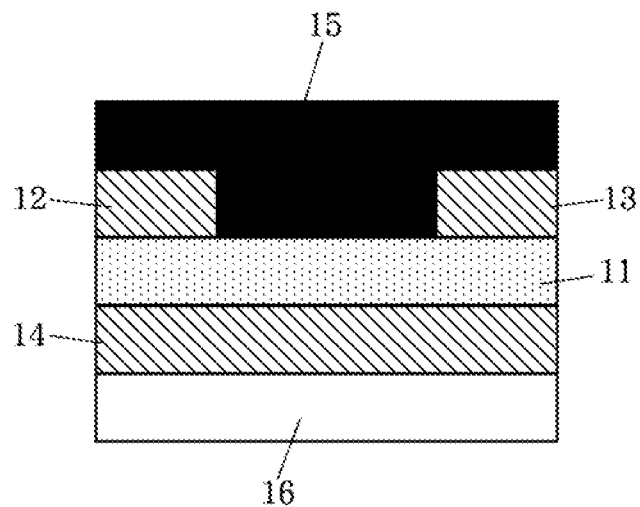
FIG. 1 is a cross-sectional view illustrating an example of the configuration of a bottom-contact organic thin-film transistor according to the present invention.

Preferred embodiments of the present invention will next be described in detail. It is, however, to be noted that the present invention is not limited to or by the following embodiments and can be practiced within a scope not departing from the gist of the present invention. A description will first be made about the organic semiconductor material of the present invention represented by the formula (1). The term "solvent" as used herein shall have both an effect of usability as a dispersion medium for a solute and an effect of solubility for a solute.

The organic semiconductor material according to the present invention is comprised of a perylene tetracarboxylic diimide derivative having a specific structure. Described specifically, as will be indicated by the below-described formula (1), the perylene tetracarboxylic diimide derivative has alkyl groups at both the end nitrogen atoms, respectively, of perylene tetracarboxylic diimide. Each alkyl group has from 1 to 3 heteroatoms, each of which is selected from an oxygen atom, sulfur atom and selenium atom. The perylene tetracarboxylic diimide ring structure contains, at each of the opposite ends thereof, two carbonyl groups in each of which an oxygen atom is bonded to a corresponding carbon atom via a double bond. As strong electron drawing property is produced by these carbonyl groups, the perylene tetracarboxylic diimide derivative acts as an n-type organic semiconductor material.

from an oxygen atom, sulfur atom or selenium atom, Y means a halogen atom or cyano group, m stands for a number of from 0 to 4, n stands for a number of from 0 to 2, and the alkyl groups represented by $R_1$ and $R_2$ may each be substituted with one or more fluorine atoms.

The derivative represented by the formula (1) is provided with a deep HOMO (Highest Occupied Molecular Orbital) energy level owing to the inclusion of the four carbonyl groups as electron withdrawing groups, and therefore, has the possibility of providing an organic thin-film transistor that can exhibit stable transistor performance despite the existence of impurities such as oxygen and water contained in the atmosphere. Owing to interaction between molecules of the skeleton structure of perylene as a polycyclic aromatic hydrocarbon, this material can also exhibit characteristics as an electron transport material. The skeleton structure of perylene is, therefore, considered to form strong stacking and to achieve high electron mobility in an organic semiconductor thin film formed by any of various film-forming processes such as vapor deposition, printing or coating.

The derivative represented by the formula (1) shows excellent solubility to an organic solvent owing to the inclusion of the alkyl groups, each of which contains from 1 to 3 heteroatoms selected from oxygen, sulfur and selenium atoms, at each of both end nitrogen atoms of perylene tetracarboxylic diimide. With the derivative, organic semiconductor thin films can, therefore, be stably formed by a printing process or coating process. As particularly preferred forms, perylene tetracarboxylic diimide derivatives having alkyl ether groups, each of which contains an oxygen atom, can be mentioned. According to a study by the present inventors, the derivative shows high solubility to an organic solvent and permits forming an organic semiconductor thin film by a solution coating process.

As the chain lengths of the respective alkyl groups forming the derivative represented by the formula (1), those to be described below are preferred. From the viewpoint of excellent solubility, preferred $R_2$ and $R_3$ in the formula (1) may each independently be a linear or branched alkyl group having from 2 to 6 carbon atoms. As derivatives having still better solubility, those of the formula (1) in which each $R_2$ is an ethyl group or propyl group can be mentioned. Insofar as each $R_1$ in the formula (1) is an alkyl group having from 1 to 20 carbon atoms, these derivatives can be used without problem to achieve the objects of the present invention. Among such derivatives, the derivatives that contain from 4 to 18 carbon atoms in each $R_1$ are particularly good in solubility, readily undergo a phase transition into a liquid crystal state in the temperature range of from 100° C. to 250° C., and can exhibit still better transistor performance. As those which can exhibit outstanding transistor performance, it is possible to mention the derivatives of the formula (1) in which each $R_1$ is an alkyl group having from 8 to 18 carbon atoms, especially the

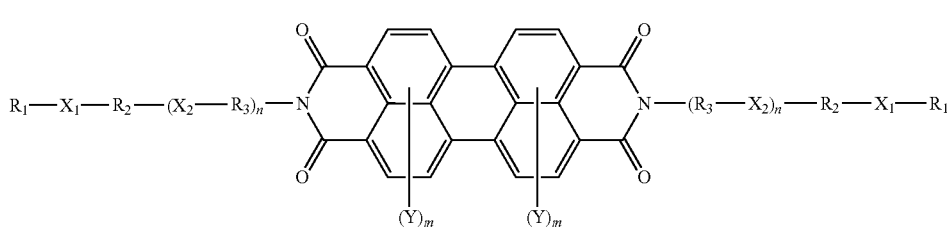

(1)

wherein $R_1$ means a linear or branched alkyl group having from 1 to 20 carbon atoms, $R_2$ and $R_3$ each independently mean a linear or branched alkyl group having from 2 to 6 carbon atoms, $X_1$ and $X_2$ each mean a heteroatom selected derivatives of the formula (1) in which each $R_1$ is an alkyl group having from 10 to 14 carbon atoms.

According to the study by the present inventors, the derivative represented by the formula (1) can be improved further in its solubility to an organic solvent by the introduction of one or more halogen atoms such as fluorine, chlorine, bromine or iodine atoms and/or one or more cyano groups into the perylene skeleton structure. Therefore, the use of a derivative having such a structure makes it possible to form a uniform film by a printing process or solution coating process, and further, to stably realize transistor characteristics in the atmosphere.

According to the study by the present inventors, the use of the derivative represented by the formula (1), in which a fluorine-substituted alkyl group is used as each of $R_1$ and $R_2$, makes it possible to prevent impurities such as water, oxygen and air from penetrating into the organic semiconductor thin film, and hence, to exhibit more stable n-type semiconductor characteristics.

The perylene tetracarboxylic diimide derivative, which constitutes the organic semiconductor material according to the present invention, can be synthesized by a known process. The perylene tetracarboxylic diimide derivative for use in the present invention can be obtained, for example, by reacting a perylene tetracarboxylic acid anhydride with the corresponding amine in an organic solvent of high boiling point or by once forming a perylene tetracarboxylic diimide into its potassium salt and then reacting it with the corresponding alkyl halide.

As amine components usable upon synthesis of the perylene tetracarboxylic diimide derivatives which constitute organic semiconductor materials according to the present invention, the below-described amine components can be mentioned. Examples include 3-methoxy-n-ethylamine, 3-methoxy-n-propylamine, 3-ethoxy-n-propylamine, 4-ethoxy-n-butylamine, 5-(n-butyloxy)-n-pentylamine, 3-(n-butyloxy)-n-propylamine, 3-(n-butyloxy)-n-hexylamine, 3-(n-heptyloxy)-n-propylamine, 3-(iso-butyloxy)-n-propylamine, 3-(sec-butyloxy)-n-propylamine, 3-(tert-butyloxy)-n-propylamine, 3-(n-octyloxy)-n-propylamine, 3-(n-decyloxy)-n-propylamine, 3-(n-dodecyloxy)-n-propylamine, 3-(n-tetradecanoxy)-n-propylamine, 3-(n-eicosanoxy)-n-propylamine, 2-(2-ethoxyethyloxy)ethylamine, 2-(2-n-butyloxy)ethylamine, 2-(2-n-hexyloxy)ethylamine, 2-(2-n-octyloxy)ethylamine, 2-(2-sec-octyloxy)ethylamine, 2-(2-butoxypropyloxy)propylamine, 2-(2-(dodecyloxy)propyloxy)propylamine, 3-(n-butylthio)propylamine, 3-(ethylthio)propylamine, 3-(n-dodecylthio)propylamine, 3-(n-dodecylselanyl)propylamine, and the like.

Taking into consideration the availability and reaction readiness of the raw materials, the semiconductor characteristics of the synthesized perylene tetracarboxylic diimide derivative, and the like, the following ones are preferred among the above-mentioned ones. Examples include 3-methoxy-n-propylamine, 3-ethoxy-n-propylamine, 5-(n-butyloxy)-n-pentylamine, 3-(n-butyloxy)-n-propylamine, 3-(n-butyloxy)-n-hexylamine, 3-(n-heptyloxy)-n-propylamine, 3-(n-octyloxy)-n-propylamine, 3-(n-decyloxy)-n-propylamine, 3-(n-dodecyloxy)-n-propylamine, 3-(n-tetradecanoxy)-n-propylamine, and 3-(n-eicosanoxy)-n-propylamine, with 3-(n-butyloxy)-n-propylamine and 3-(n-dodecyloxy)-n-propylamine being more preferred.

As perylene tetracarboxylic acid anhydrides usable upon synthesis of perylene tetracarboxylic diimide derivatives which constitute organic semiconductor materials according to the present invention, the below-described perylene tetracarboxylic acid anhydrides can be mentioned. Examples include unsubstituted 3,4:9,10-perylene tetracarboxylic acid anhydride, 1,7-dicyano-3,4:9,10-perylene tetracarboxylic acid anhydride, 1,7-dichloro-3,4:9,10-perylene tetracarboxylic acid anhydride, 1,7-difluoro-3,4:9,10-perylene tetracarboxylic acid anhydride, 1,6,7,10-tetrafluoro-3,4:9,10-perylene tetracarboxylic acid anhydride, and the like. Taking into consideration the availability and reaction readiness of the raw materials, the semiconductor characteristics of the synthesized perylene tetracarboxylic diimide derivative, and the like, it is preferred to use, among those described above, the unsubstituted perylene tetracarboxylic acid anhydrides with no substituent group or groups introduced on their perylene skeletons.

For use in the organic thin-film transistor, it is preferred to use the organic semiconductor material (derivative) in a purified form. A reduction of impurities in the material will decrease causes that inhibit the movement of electrons through the organic semiconductor thin film to be formed with the material, and will provide the resulting organic thin-film transistor with an increased electron mobility, and therefore, with improved transistor performance. No particular limitation is imposed on the method for increasing the purity of the material, but the use of a purification method such as preparative chromatography, recrystallization or sublimation purification or combined use thereof can provide the material with increased purity.

In the present invention, more preferred among the derivatives represented by the formula (1) are an N,N'-bis(3-($R_1$-oxy)-ethyl)-3,4:9,10-perylene tetracarboxylic diimide derivative represented by the following formula (2) and an N,N'-bis(3-($R_1$-oxy)-n-propyl)-3,4:9,10-perylene tetracarboxylic diimide derivative represented by the following formula (3).

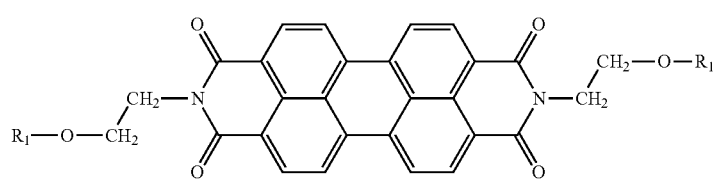

(2)

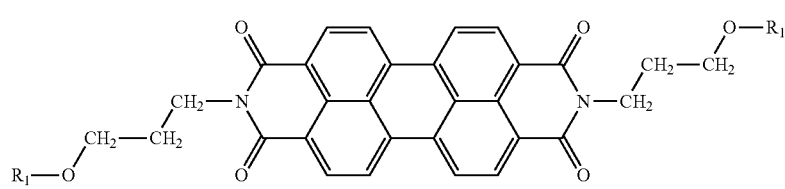

(3)

wherein $R_1$ means a linear alkyl group or branched alkyl group having from 1 to 20 carbon atoms.

In the present invention, particularly preferred is N,N'-bis(3-(n-dodecyloxy)-n-propyl)-3,4:9,10-perylene tetracarboxylic diimide represented by the following formula (4):

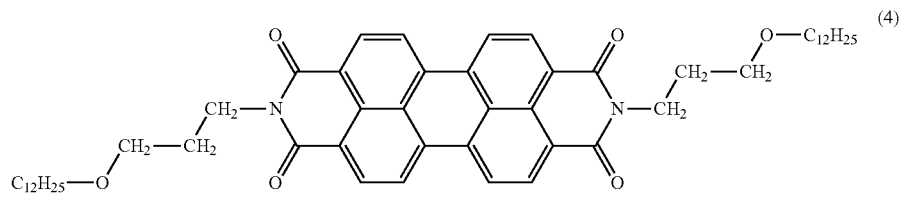

The above-mentioned derivative, which is represented by the formula (1) and characterizes the present invention, exhibits characteristics as an n-type organic semiconductor material, and the use of the derivative as an organic semiconductor thin film makes it possible to fabricate an organic thin-film transistor of excellent performance.

A more detailed description will hereinafter be made about organic thin-film transistors according to the present invention. It should, however, be borne in mind that the present invention is not limited to these structures.

As the structure of an organic thin-film transistor, the MIS structure (Metal-Insulator-Semiconductor structure) that a gate electrode is insulated by an insulating film is often used in general. An organic thin-film transistor to which the present invention can be applied has an organic semiconductor layer formed of an organic semiconductor thin film, and is further comprised of a source electrode, a drain electrode, a gate electrode and a gate insulating layer. The organic thin-film transistor according to the present invention is characterized in that the organic semiconductor thin film is made of the organic semiconductor material comprised of the compound (the derivative represented by the formula (1)) having the alkyl ether groups at both ends of the skeleton structure formed of perylene tetracarboxylic acid diimide.

Figure 2:
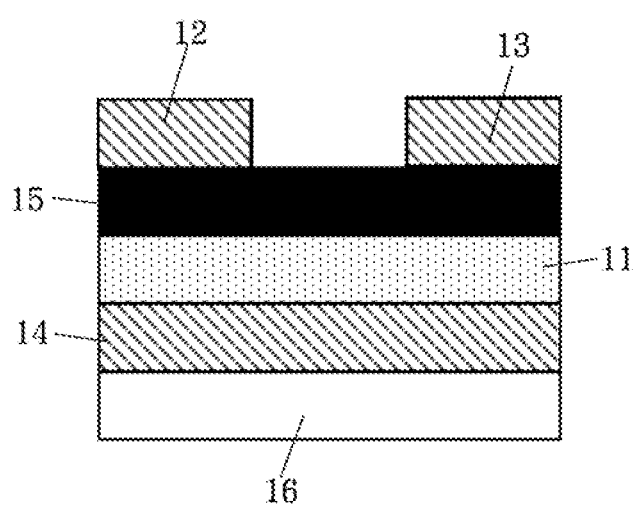
FIG. 2 is a cross-sectional view illustrating an example of the configuration of a top-contact organic thin-film transistor according to the present invention.

A description will next be made about the configuration of the organic thin-film transistor according to the present invention. FIGS. 1 and 2 are cross-sectional views illustrating different examples of the construction of the organic thin-film transistor according to the present invention, respectively. In the configuration of the organic thin-film transistor as illustrated in FIG. 1, a gate electrode 14 is arranged on a substrate 16, an insulating layer 11 is stacked on the gate electrode, a source electrode 12 and a drain electrode 13 are formed with a predetermined interval therebetween on the insulating layer 11, and further, an organic semiconductor thin film 15 is stacked on the insulating layer 11, source electrode 12 and drain electrode 13 to form a so-called bottom-gate, bottom-contact configuration. In the configuration of the organic thin-film transistor as illustrated in FIG. 2, a gate electrode 14 is arranged on a substrate 16, an insulating layer 11 is stacked on the gate electrode, an organic semiconductor thin film 15 is stacked on the insulating layer 11, and further, a source electrode 12 and a drain electrode 13 are stacked with a predetermined interval therebetween on the organic semiconductor layer 15 to form a so-called bottom-gate, top-contact configuration.

The transistor device having one of such configurations performs a switching operation when a voltage is applied between the gate electrode and the source electrode and by the voltage so applied, the organic semiconductor thin film forms a channel region to control an electric current that flows between the source electrode and the drain electrode.

The organic semiconductor thin film comprised of the organic semiconductor material according to the present invention can be formed by vapor deposition or sputtering. However, its formation is not limited to such a process, but can also use a solution coating process or printing process. The solution coating process forms the organic semiconductor thin film by coating a solution in which the organic semiconductor material is dissolved in a solvent. The solution coating process or printing process is useful, because it can realize further simplification of facilities and a further reduction in cost, can form the organic semiconductor thin film over a large area, and at the same time, has the possibility of forming, as the organic semiconductor thin film, a film inherently reduced in crystal grain boundaries, deficiencies and defects that are significant especially when formed by vapor deposition. Similarly, it is useful to form the organic semiconductor thin film by coating a dispersion in which the organic semiconductor material is dispersed in a solvent and/or water. The use of the organic semiconductor material according to the present invention makes it possible to form the organic semiconductor thin film, for example, by a solution coating process such as spin coating, or a printing process such as inkjet printing, screen printing, planographic printing, letterpress printing, or intaglio printing.

No particular limitation is imposed on the solvent to be used when the organic semiconductor thin film according to the present invention is formed by the solution coating process or printing process, insofar as a solution of adequate concentration can be obtained. Examples include halogenated hydrocarbon solvents such as chloroform, dichloroethane, chlorobenzene, dichlorobenzene, trichlorobenzene and chloronaphthalene; ketone solvents such as acetone, methyl ethyl ketone and methyl isobutyl ketone; ester solvents such as ethyl acetate and butyl acetate; ether solvents such as diethyl ether, dioxane and tetrahydrofuran; aromatic hydrocarbon solvents such as toluene, xylene and ethylbenzene; and aprotic polar solvents such as tetrahydrofuran, sulfolane, N,N-dimethylformamide, N-methyl-2-pyrrolidone and dimethylsulfoxide. These solvents may be used either singly or in a combination of two or more thereof.

The organic semiconductor thin film of the present invention formed as described above can be provided with improved transistor characteristics by subjecting it to heat treatment at a temperature of from 100 to 250° C. A description will hereinafter be made in this regard.

The phase change of the organic semiconductor thin film of the present invention by a change in temperature is considered to occur for the structure of the above-described specific derivative that forms the organic semiconductor thin film. Described specifically, owing to the inclusion of from 1 to 3 heteroatoms in each alkyl chain bonded to the perylene tetracarboxylic diimide group of the derivative, the organic semiconductor thin film shows a phase transition into a liquid crystal phase (smectic liquid crystal) in a temperature range of from 100° C. to 200° C. Phase changes of long-chain alkylperylene tetracarboxylic diimides are described in an already known document (C. W. Struijk, et al., J. Am. Chem. Soc., 122, (2000)).

Figure 7:
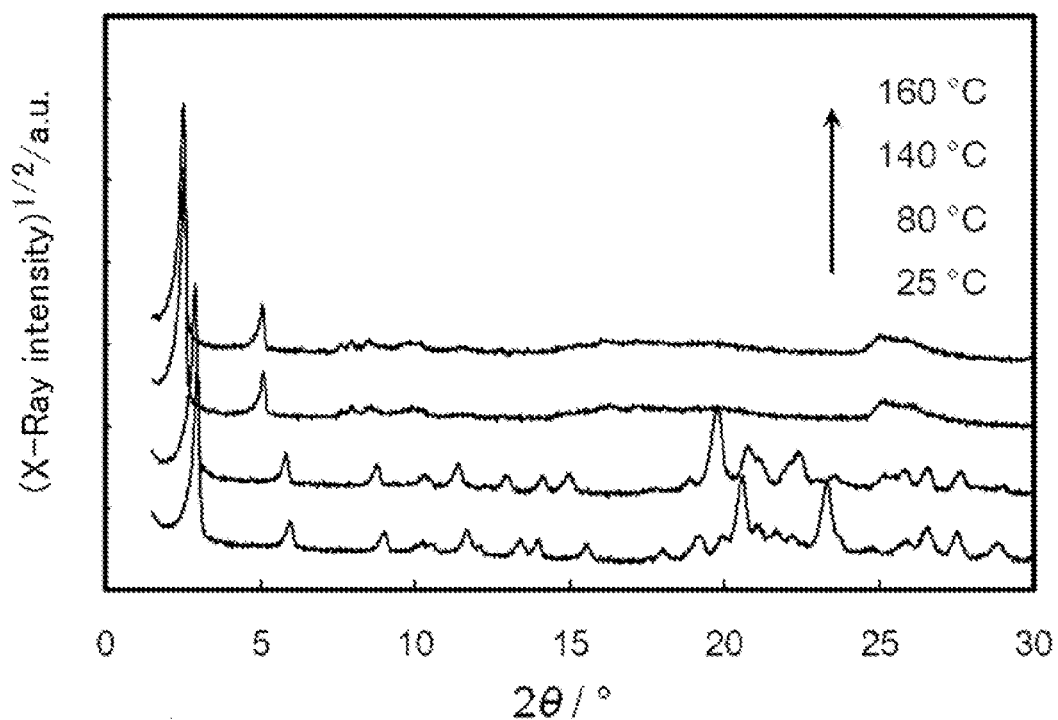
FIG. 7 is a diagram showing X-ray diffraction patterns of organic semiconductors according to the present invention.

In FIG. 7, powder X-ray diffraction patterns of N,N'-bis(3-(n-dodecyloxy)-n-propyl)-3,4:9,10-perylene tetracarboxylic diimide, which is particularly suited as the organic semiconductor material according to the present invention, at 25° C., 80° C., 140° C. and 160° C. are shown.

Figure 5:
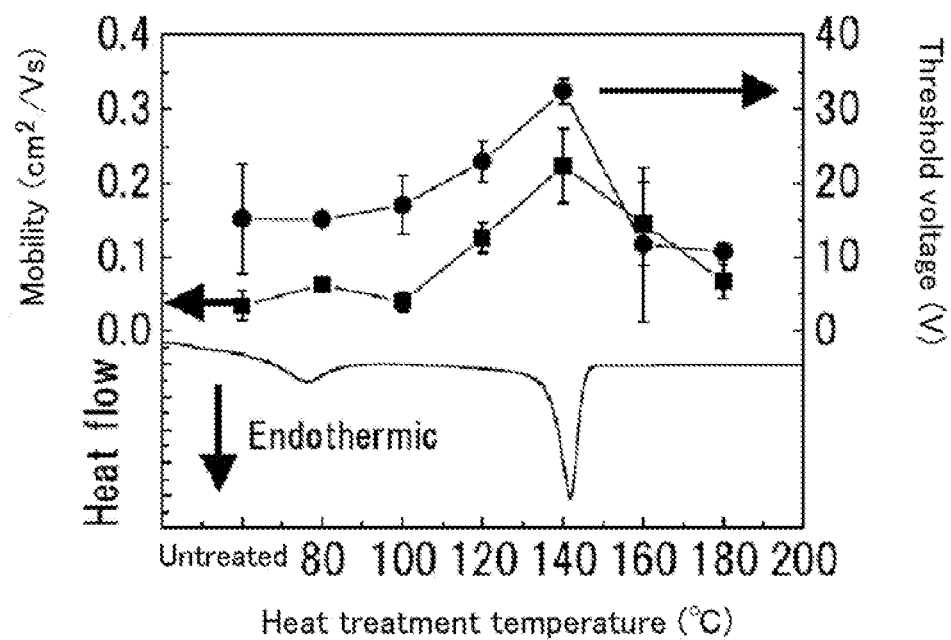
FIG. 5 is a diagram showing the mobility and heat treatment temperature dependency of an organic thin-film transistor according to the present invention.

As indicated in FIG. 7, diffraction patterns associated with a stacked structure and crystalline structure are observed at 25° C. and 80° C. At each of 140° C. and 160° C., however, a peak ascribable to the stacked structure is observed but a peak from the crystalline structure in the stacked structure is very weak and is substantially flat. In FIG. 5, the results of differential scanning calorimetry of the organic semiconductor material are shown. As indicated in FIG. 5, an endothermic peak is observed around 135° C. to 145° C. The organic semiconductor material is considered to have undergone a phase change (phase transition) from a crystalline state into a liquid crystal state in the temperature range.

The present inventors reported that the heat treatment of an organic semiconductor thin film, which is formed of a perylene tetracarboxylic diimide derivative, around its phase change temperature provides the resulting organic thin-film transistor with improved transistor performance (see Patent Document 2 cited above).

About the principle that the transistor performance is improved by subjecting the organic semiconductor thin film, which is formed of the organic semiconductor material according to the present invention, to the heat treatment, the present inventors believe as will be described hereinafter. An organic semiconductor thin film formed by a vapor deposition process or a solution coating process has a polycrystalline structure formed of microcrystals aggregated together and includes many crystal grain boundaries and defects. The existence of these crystal grain boundaries and defects inhibits the transport of electrons. On the other hand, the thin film formed of the organic semiconductor material according to the present invention takes a liquid crystal state when subjected to heat treatment, but takes a crystalline state again when cooled. It is considered that upon taking the crystalline state again, the transistor characteristics have been improved, in other words, the electron mobility has been increased by a combined action of [1] the formation of a strongly stacked state through a rearrangement of molecules, [2] the elimination of impurities upon crystallization, [3] an increase in grain size and a reduction in crystal grain boundaries, defects and deficiencies, [4] enhanced close contact with electrodes, and so on.

The temperature of the heat treatment for the organic semiconductor thin film according to the present invention may preferably be in the range of from 100° C. to 250° C. A heat treatment temperature lower than 100° C. may not provide sufficiently improved transistor performance, and moreover, causes variations in performance depending on the temperature environment in which the resulting transistor is used. A heat treatment temperature higher than 250° C., on the other hand, may cause deteriorations in individual materials, and moreover, is disadvantageous from the standpoint of cost. Heat treatment temperatures outside the above-described range are, therefore, not preferred. As a particularly preferred temperature, heat treatment at from 100° C. to 200° C. is especially preferred in view of the possibility of formation of the organic transistor on a flexible plastic substrate.

Concerning the atmosphere of an environment in which the heat treatment is conducted, the heat treatment can be conducted in the atmosphere or an inert gas or under reduced pressure. It is preferred to conduct the heat treatment under an atmosphere of reduced pressure or an atmosphere of inert gas, because the individual materials can be protected from deterioration, oxidation or the like.

No particular limitation is imposed on a heat treatment method, and an oven, hot roll, hot press or the like can be used. As an alternative, the heat treatment and drying can be conducted together in a drying zone after the organic semiconductor thin film is formed by printing. Although no particular limitation is imposed on the time of the heat treatment insofar as the organic semiconductor thin film is allowed to reach a predetermined temperature, the time of the heat treatment may desirably be 24 hours or shorter as long-time heat treatment accelerates a deterioration of the substrate.

A description will next be made about the substrate to be used upon forming the organic thin-film transistor of the present invention by using the organic semiconductor thin film. As the substrate, any substrate can be used insofar as it is a material having insulating properties. The organic thin-film transistor can be fabricated using an inorganic material such as glass or alumina or a plastic substrate such as a polyimide film, polyester film, polyethylene film, polystyrene film, polypropylene film or polycarbonate film. The use of a plastic substrate makes it possible to fabricate a lightweight, flexible organic thin-film transistor of excellent impact resistance. These substrates may be used either singly or in combination. It is to be noted that, when an electrically-conductive substrate, for example, a silicon substrate is used, the substrate can also serve as a gate electrode.

A description will next be made about the gate insulating layer that forms the organic thin-film transistor according to the present invention. Examples of a material that forms the gate insulating layer include, but are not specifically limited to, inorganic materials such as $SiO_2$, $ZrO_2$, $Ta_2O_5$, $La_2O_3$, $Al_2O_3$ and $HfO_2$. As polymer-based insulating film materials, on the other hand, organic materials such as polyimides, polymethyl methacrylate, polyvinyl alcohol, polyvinylphenol, polyvinyl chloride, polyacrylonitrile, polyvinylidene fluoride, polyethylene terephthalate, polyethersulfone and polycarbonates can be used. These insulating materials useful as gate insulating layers may be used either singly or in combination.

No particular limitation is imposed on a process for forming such agate insulating layer. Illustrative are dry processes such as vapor deposition, CVD, sputtering and atmospheric-pressure plasma processing; and wet processes such as coating processes such as spray coating, spin coating, blade coating, dip coating, casting, roll coating, bar coating, die coating, air knife coating, slide hopper coating and extrusion, various printing processes, and inkjet printing. Depending on the properties of materials to be used, a desired process can be selected and applied as desired. For example, $SiO_2$ may be formed as a layer on a silicon substrate by thermal oxidation, steam oxidation or plasma oxidation.

A gate insulating layer may be hydrophobized by chemical surface treatment to improve the compatibility between the gate insulating layer and an organic semiconductor thin film, so that the organic semiconductor thin film can be uniformly formed to reduce a leak current. Although not specifically limited, such a hydrophobizing layer can be formed by solution coating or vapor deposition of a silane coupling agent such as, for example, OTS (octadecyltrichlorosilane), ODS (octadecyltrimethoxysilane) or HMDS (hexamethyldisilazane) on the gate insulating layer.

A description will next be made about electrode materials for forming the organic thin-film transistor according to the present invention. As electrode materials for the source electrode, drain electrode and gate electrode, materials having electrical conductivity are used. Usable examples include metal materials such as gold, silver, copper, platinum, aluminum, lithium, sodium, potassium, magnesium, calcium, titanium, indium, palladium, manganese, molybdenum, magnesium, calcium, barium, chromium, tungsten, tantalum, nickel, cobalt, copper, iron, lead and tin, and alloys of these metal materials; electrically-conductive oxides such as $InO_2$, $ZnO_2$, $SnO_2$, ITO (indium tin oxide) and IZO (indium zinc oxide); carbon materials such as carbon black, fullerene, carbon nanotubes and graphite; and electrically-conductive high-molecular compounds. More preferred are gold, aluminum, magnesium, calcium, ITO, IZO and gold/chromium alloy as they each have small electric resistance at the surface of contact with the organic semiconductor thin film.

No particular limitation is imposed on a process for the formation of these electrodes. For example, they can be formed by using a process such as a printing process making use of a dispersion of an electrically-conductive material in a solution, a printing process making use of a solution of an electrically-conductive material in a solution, a vapor deposition process, or a sputtering process.

The source electrode and the drain electrode are arranged opposite each other. The inter-electrode distance (channel length) is one of parameters that determine transistor characteristics. An inter-electrode distance (channel length) not greater than 100 μm is generally usable without problem, with 50 μm or smaller being preferred. As the width between the source electrode and, the drain electrode (channel width), any width can be used without any particular limitation, but 1 mm or smaller is preferred. However, a still longer channel width may be formed when the electrodes are formed, for example, in a comb-shaped structure. The source electrode and drain electrode so formed can be used without problem insofar as they have a thickness in a range of from several nanometers to several hundreds micrometers. More preferably, however, the thicknesses of the source electrode and drain electrode may range from 30 nm to 30 μm.

The organic thin-layer transistor according to the present invention contains, in its organic semiconductor thin film, at least one of the above-described specific perylene tetracarboxylic diimide derivatives that characterize the present invention. These derivatives may be used either singly or in a combination of two or more thereof. The derivatives may also be used in combination with one or more of perylene and its derivatives and naphthalene diimide and its derivatives, although the content of the organic semiconductor material according to the present invention should preferably account for 90 mass % or higher.

The organic thin-film transistor according to the present invention may be provided on the entire part or a part of its outer circumferential surface with a gas barrier layer to reduce the effects of oxygen, water and the like in the atmosphere. Examples of a material that forms such a gas barrier layer include polyvinyl alcohol, ethylene-vinyl alcohol copolymer, polyvinyl chloride, polyvinylidene chloride, and the like.

The organic thin-film transistor according to the present invention can be evaluated for transistor characteristics by electron mobility ($cm^2/Vs$), ON/OFF ratio and threshold voltage (V). To obtain a large current through the organic thin-film transistor, it is particularly important that its electron mobility has a large value. The electron mobility may desirably be 0.01 $cm^2/Vs$ or higher. When organic thin-film transistors have an electron mobility of 0.01 $cm^2/Vs$, they can be used as memory cells or drive elements for electron paper displays. When organic thin-film transistors have an electron mobility of 0.1 $cm^2/Vs$ or higher, they can be used, for example, as drive elements for active matrices as replacements for amorphous silicon transistors.

EXAMPLES

Examples of the present invention will hereinafter be described to illustrate the present invention in more detail.

Synthesis Example 1

Synthesis of Compound A

Perylene tetracarboxylic acid anhydride (3.92 g) and 3-(n-dodecyloxy)-n-propylamine (9.72 g) were dispersed in imidazole (40 g), followed by stirring at 160° C. for 4 hours under a nitrogen gas stream. The reaction mixture was allowed to cool, and was then filtered. The resulting filter cake was washed with a dilute solution of hydrochloric acid in methanol and with water in this order. Subsequently, the filter cake was dried to afford N,N'-bis(3-(n-dodecyloxy)-n-propyl)-3,4:9,10-perylene tetracarboxylic diimide represented by the below-described formula (4) (5.90 g, yield: 70%). The above-afforded compound was isolated by column chromatography, and was purified by recrystallization to provide it as a compound A. Endothermic peaks of the compound A as measured by differential scanning calorimetry (DSC) (measured from room temperature to 250° C.) appeared at 81° C. and 144.3° C. The compound A may hereinafter be called "PTCDI-C3-O—C12".

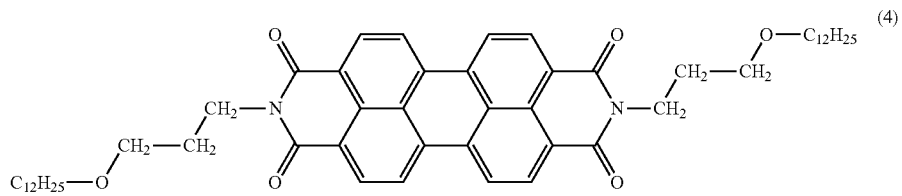

(4)

Synthesis Example 2

Synthesis of Compound B

In a similar manner as in Synthesis Example 1 except that 3-(n-dodecyloxy)-n-propylamine (9.72 g) employed in Synthesis Example 1 was changed to 3-(n-butyloxy)-n-propylamine (5.24 g), N,N'-bis(3-(n-butyloxy)-n-propyl)-3,4:9,10-perylene tetracarboxylic diimide was afforded (4.95 g, yield: 80%). The above-afforded compound was isolated by column chromatography, and was purified by recrystallization to provide it as a compound B. An endothermic peak of the compound B as measured by differential scanning calorimetry (DSC) (measured from room temperature to 250° C.) appeared at 168° C. The compound B may hereinafter be called "PTCDI-C3-O—C4".

Synthesis Example 3

Synthesis of Compound C

In a similar manner as in Synthesis Example 1 except that 3-(n-dodecyloxy)-n-propylamine employed in Synthesis Example 1 was changed to 3-(2-ethylhexyloxy)-n-propylamine, N,N'-bis(3-(2-ethylhexyloxy)-n-propyl)-3,4:9,10-perylene tetracarboxylic diimide was afforded as a compound C (yield: 85%). The above-afforded compound was isolated by column chromatography, and was purified by recrystallization to provide it as the compound C. endothermic peak of the compound C as measured by differential scanning calorimetry (DSC) (measured from room temperature to 250° C.) appeared at 159° C. The compound C may hereinafter be called "PTCDI-C3-O—C2C6".

Synthesis Example 4

Synthesis of Compound D

Syntheses were conducted by the following procedures 1) to 3).

1) Synthesis of 3,4,9,10-perylene tetracarboxylic acid monopotassium salt (I)

To a 500-mL, 3-neck flask, a 85% aqueous solution of KOH (280 g) and perylene tetracarboxylic acid anhydride (20 g) were added, followed by stirring at 90° C. for 3 hours. A 10% aqueous solution of $H_3PO_4$ was added dropwise, followed by stirring at 90° C. for 1 hour. After the resulting mixture was allowed to cool to room temperature, deposits were collected by filtration. The resulting filter cake was washed with water, and was then dried for 1 day to afford 3,4,9,10-perylene tetracarboxylic acid monopotassium salt (I) with a yield of 95% (21 g). This compound will be called simply "the monopotassium salt (I)".

2) Synthesis of monoimide (II)

To a 200-mL, 3-neck flask, the monopotassium salt (I) (4.5 g) afforded as described above, 3-dodecyloxypropylamine (7.3 g) and a mixed solution (60 mL) of propanol and water were added. The contents were then reacted under stirring at room temperature for 6 hours. Subsequently, the contents were reacted further at 90° C. for 6 hours. After completion of the reaction, the reaction mixture was allowed to cool to room temperature, a 10% aqueous solution of HCl (80 g) was added, and stirring was then conducted at room temperature for 1 hour. Subsequently, deposits were collected by filtration, and the resulting filter cake was washed with water. To the filter cake so obtained, a 10% aqueous solution of KOH (400 mL) was added. Subsequent to stirring at 60° C. for 1 hour, an 8% aqueous solution of KCl (40 g) was added, and the resulting precipitates were collected by filtration. The thus-obtained filter cake was washed with a dilute solution of hydrochloric acid in water and with water in this order. Subsequently, the filter cake was dried to afford a monoimide (II) (N-(3-dodecyloxypropyl)perylene tetracarboxylic monoanhydride monoimide) with a yield of 70%.

3) Synthesis of diimide (II)

To a 100-mL, 3-neck flask, the monoimide (II) (3.1 g) afforded as described above, 3-butoxypropylamine (2.0 g) and NMP (N-methyl-2-pyrrolidone, 40 mL) were added, followed by stirring under heating at from 160 to 170° C. for 6 hours. The reaction mixture was allowed to cool back to room temperature, and was then filtered. The resulting filter cake was washed with methanol and then with water, and thereafter, was dried. The thus-obtained compound was isolated and purified by column chromatography, and was recrystallized to afford a diimide (III) (N-(3-dodecyloxypropyl)-N'-(3-butoxypropyl)perylene tetracarboxylic diimide) as a compound D with a yield of 75%. The above-described reactions will be shown together below. The compound D may hereinafter be called "PTCDI-C3-O—C4,C12".

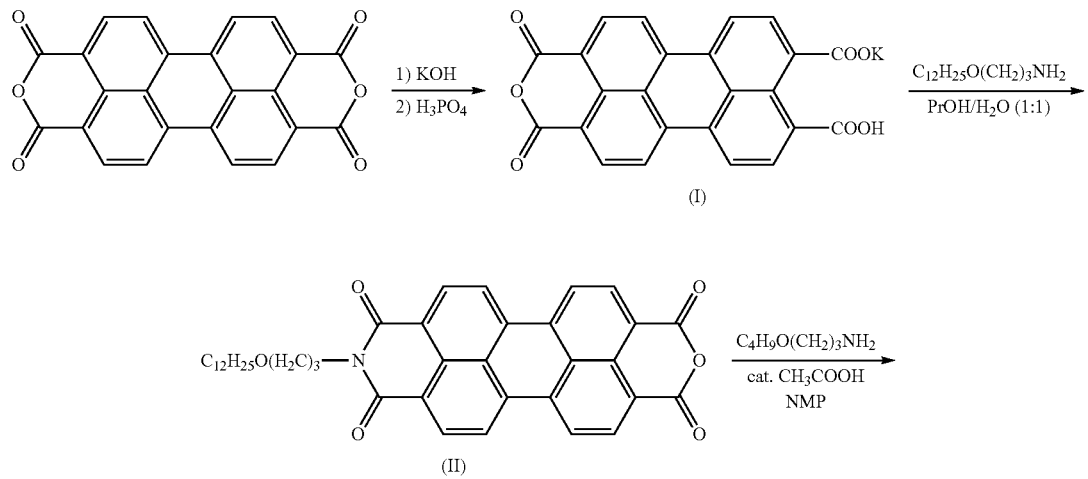

-continued

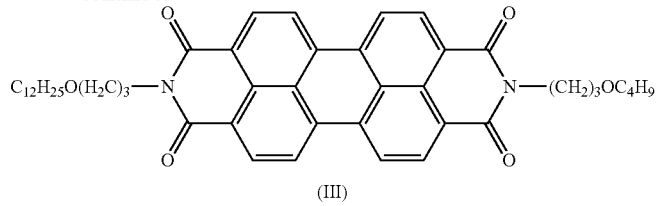

(III)

An endothermic peak of the above-afforded compound D as measured by differential scanning calorimetry (DSC) (measured from room temperature to 250° C.) appeared at 124.5° C.

Synthesis Example 5

Synthesis of Mixture E

In a similar manner as in Synthesis Example 1 except that 3-(n-dodecyloxy)-n-propylamine was changed to a 1:1 (molar ratio) mixture of 3-(n-dodecyloxy)-n-propylamine and 3-(n-tetradecyloxy)-n-propylamine, a mixture E was afforded (yield: 85%). The mixture E was fractionated by column chromatography, and was purified by recrystallization to isolate compounds E1, E2 and E3. Those compounds E1, E2 and E3 were identified to have the below-described structures. As a result, the ratio of the respective compounds in the mixture E was confirmed to be the compound E1:the compound E2:the compound E3=1:2:1. Endothermic peaks of the mixture E as measured by differential scanning calorimetry (DSC) (measured from room temperature to 250° C.) appeared at 122° C. and 140° C. This mixture E may hereinafter be called "PTCDI-C3-O—C12,C14".

carboxylic diimide with no heteroatom contained in its structure was afforded (yield: 85%). The above-afforded compound was isolated by column chromatography, and was purified by recrystallization to provide it as a compound F. No endothermic peak was observed by differential scanning calorimetry (DSC) of the compound F (measured from room temperature to 250° C.). The compound F may hereinafter be called "PTCDI-C2-C8".

Evaluation of Thin-Film Transistors

Electrical characteristics of each thin film transistor were measured at room temperature under a vacuum by a semiconductor device analyzer ("B1500A") manufactured by Agilent Technologies, Inc. $I_D$ (drain current)-$V_D$ (source-drain voltage) characteristics, in other words, transfer characteristics were measured by sweeping the drain voltage $V_D$ from 0 to 100 V under respective conditions that the $V_G$ (gate voltage) was applied at 100 V, 80 V, 60 V, 40 V and 20 V, respectively. On the other hand, $I_D$-$V_G$ characteristics, in other words, output characteristics were measured by sweeping $V_G$ from 0 to 100 V at $V_D$=100 V.

From the linear region of $(I_D)^{1/2}$-$V_G$ characteristics and the equation (1), the mobility was calculated.

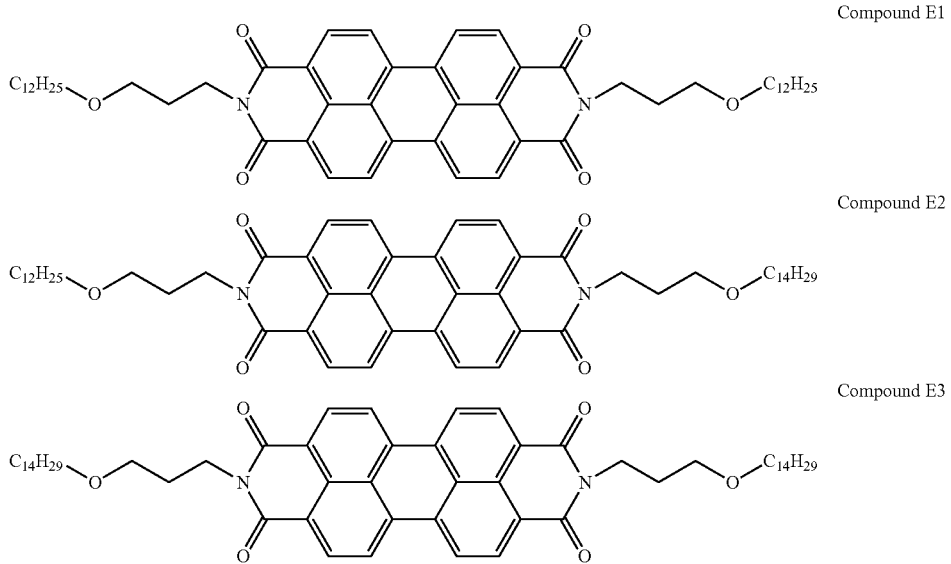

Synthesis Example 6

Synthesis of Compound F

In a similar manner as in Synthesis Example 1 except that 3-(n-dodecyloxy)-n-propylamine was changed to 2-ethylhexylamine, N,N'-bis(2-ethylhexyl)-3,4:9,10-perylene tetra- $$I_D = \frac{W}{2L} C_i \mu (V_G - V_T)^2 \quad \text{Equation (1)}$$

where $C_i$ is the capacitance (nF/cm$^2$) of a gate dielectric, and $V_T$ is a threshold voltage. Based on the slope of $(ID)^{1/2}$-$V_G$ characteristics, the field effect mobility (μ) was determined by using the equation (1), and from the intercept of the fitting line with the X-axis, the threshold voltage ($V_T$) was calculated.

Example 1

Fabrication of Organic Thin-Film Transistors with Compound A (PTCDI-C3-O—C12)

A silicon substrate, which had on a surface thereof a silicon oxide film (thickness: 200 nm) to be used as a gate insulating layer, was provided. An organic semiconductor thin film comprised of the compound A afforded in Synthesis Example 1 was formed on the silicon oxide film by an evaporation deposition process (deposition rate: 2 [nm/sec]) to give a thickness of 30 nm. Through a shadow mask, a pattern of gold electrodes (30 nm) was then formed as source/drain electrodes to fabricate top-contact organic thin-film transistors. At that time, the channel length and channel width were set at 100 μm and 2,000 μm, respectively.

Figure 3:
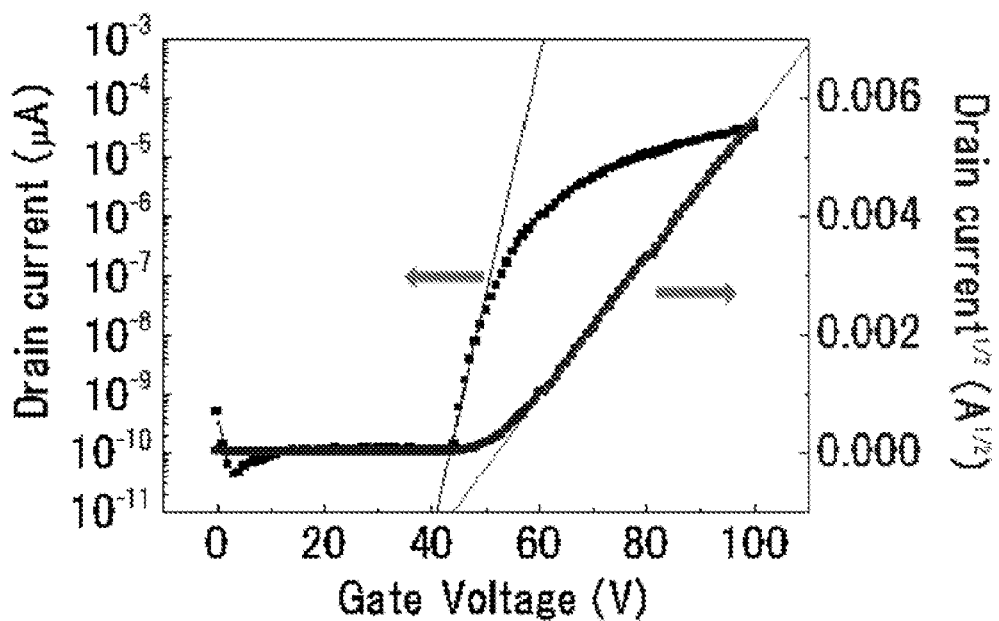
FIG. 3 is a diagram showing a relationship between output characteristics (drain current and gate voltage) of the organic thin-film transistor of Example 1.
Figure 4:
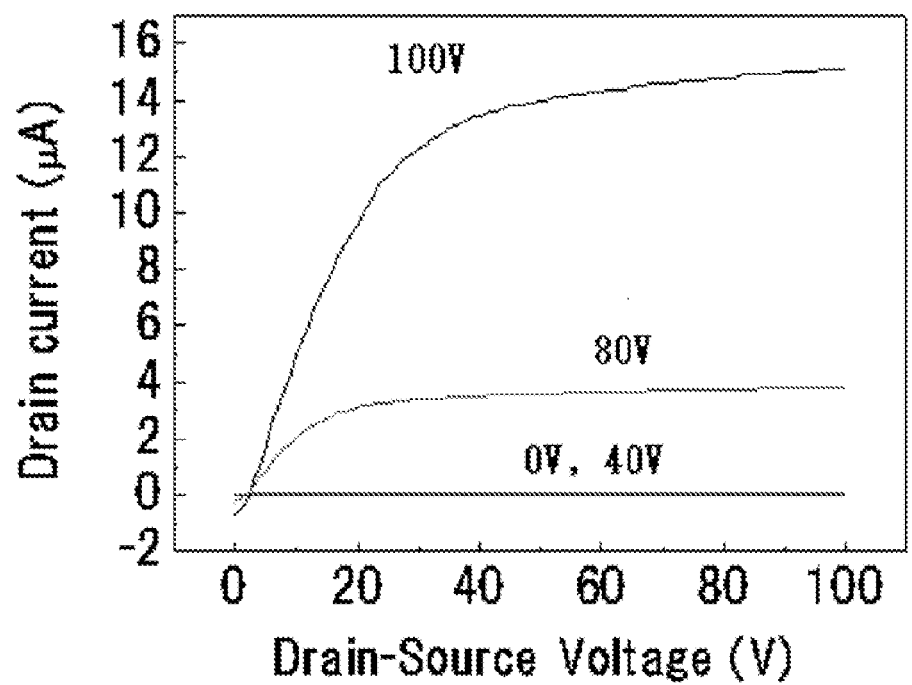
FIG. 4 is a diagram showing a relationship between transfer characteristics (drain current and drain voltage) of the organic thin-film transistor of Example 1.

With respect to some of the transistors obtained as described above, the $I_D$-$V_D$ characteristics were measured by sweeping the source-drain voltage ($V_D$) from 0 to 100 V under respective conditions that the $V_G$ (gate voltage) was applied at 100 V, 80 V, 60 V, 40 V and 20 V, respectively. On the other hand, the $I_D$-$V_G$ characteristics were measured by sweeping $V_G$ from 0 to 100 V at $V_D$=100 V. The relationship between the drain current and the gate voltage, in other words, the output characteristics as obtained as a result of the measurement is shown in FIG. 3, while the relationship between the drain current and the drain voltage, in other words, the transfer characteristics as obtained as a result of the measurement are shown in FIG. 4. As pronounced saturation regions are observed on the drain current-drain voltage curves in the $I_D$-$V_D$ characteristics, it has been demonstrated that these transistors are drivable as field-effect transistors having typical n-type characteristics. The electron mobility, threshold voltage value and ON/OFF ratio calculated from the $(I_D)^{1/2}$-$V_G$ characteristics were $3.3 \times 10^{-2}$ cm$^2$/Vs, 15 V and $10^5$, respectively.

Example 2

Fabrication of Organic Thin-Film Transistors with Compound B (PTCDI-C3-O—C4)

In this example, the compound B (N,N'-bis(3-(n-butyloxy)-n-propyl)-3,4:9,10-perylene tetracarboxylic diimide) afforded in Synthesis Example 2 was used in place of the compound A employed in Example 1. In a similar manner as in Example 1, top-contact organic thin-film transistors each having an organic semiconductor thin film comprised of the compound B were fabricated. With respect to these transistors, the $I_D$-$V_D$ characteristics and $I_D$-$V_G$ characteristics were measured in a similar manner as in Example 1. As a result, it has been demonstrated that these transistors are drivable as field-effect transistors having typical n-type characteristics. The electron mobility, threshold voltage value and ON/OFF ratio calculated from the $(I_D)^{1/2}$-$V_G$ characteristics were $3.8 \times 10^{-3}$ cm$^2$/Vs, 10 V and $10^5$, respectively.

Example 3

Fabrication of Organic Thin-Film Transistors with Compound A (PTCDI-C3-O—C12)

In this example, a silicon substrate, which had on a surface thereof a silicon oxide film (thickness: 200 nm) to be used as a gate insulating layer, was provided. An ITO film (150 nm) was formed by sputtering, and using photolithography and wet etching, a pattern of source electrodes and drain electrodes was formed. At that time, the channel length and channel width were 100 μm and 2,000 μm, respectively. Subsequently, the compound A employed in Example 1 was dissolved in chloroform to give a concentration of 0.25%. Using the solution, an organic semiconductor thin film was formed on the silicon substrate by a spin coater (1,500 rpm/60 s), followed by drying for 1 hour under reduced pressure in a vacuum.

With respect to some of the transistors obtained as described above, their transistor characteristics were measured as in Example 1. As a result, it has been demonstrated that these transistors are drivable as field-effect transistors having typical n-type characteristics. The transistor characteristic value, threshold voltage value and ON/OFF ratio calculated from the $(I_D)^{1/2}$-$V_G$ characteristics were $2.4 \times 10^{-2}$ cm$^2$/Vs, 56 V and $10^5$, respectively.

Examples 4 to 8

Using plural ones of the devices fabricated in Example 1, they were subjected to heat treatment for 2 hours at the predetermined temperatures shown in Table 1, respectively. The thus-treated devices were provided as the devices of Examples 4 to 8. Transistor characteristics of each device so obtained, as calculated from its $(I_D)^{1/2}$-$V_G$ characteristics, are shown in Table 1 and FIG. 5.

TABLE 1

Relationship between Heat Treatment Temperature and Transistor Characteristics (Compound A + Vapor Deposition)

| | Heat treatment temperature | Mobility (cm$^2$/Vs) | Threshold voltage (V) | ON/OFF ratio |
|---|---|---|---|---|
| Example 1 | Untreated | $3.3 \times 10^{-2}$ | 15 | $10^5$ |
| Example 4 | 100° C. | $3.4 \times 10^{-2}$ | 15 | $10^5$ |
| Example 5 | 120° C. | $1.3 \times 10^{-1}$ | 17 | $10^5$ |
| Example 6 | 140° C. | $2.8 \times 10^{-1}$ | 31 | $10^5$ |
| Example 7 | 160° C. | $1.4 \times 10^{-1}$ | 12 | $10^5$ |
| Example 8 | 180° C. | $6.3 \times 10^{-2}$ | 10 | $10^5$ |

Figure 6:
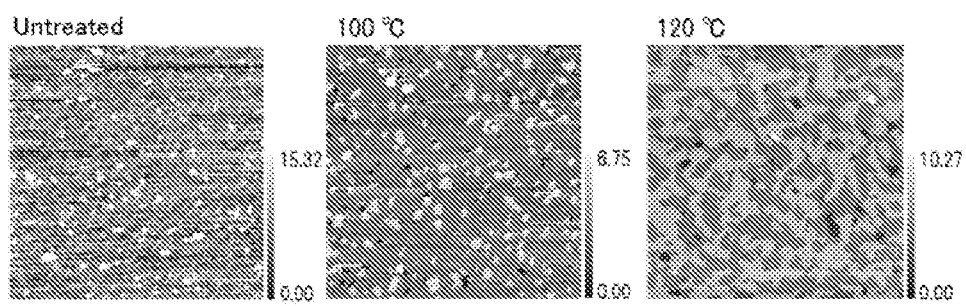
FIG. 6 shows pictures illustrating the growth of grain size in an organic semiconductor thin film through heat treatment.

Growth of grain size in the organic semiconductor thin films through the heat treatment is shown in FIG. 6.

Examples 9 to 13

Using plural ones of the devices fabricated in Example 3, they were subjected to heat treatment for 1 hour at the predetermined temperatures shown in Table 2, respectively. The thus-treated devices were provided as the devices of Examples 9 to 13. Transistor characteristics of each device so obtained, as calculated from its $(I_D)^{1/2}$-$V_G$ characteristics, are shown in Table 2.

TABLE 2

Relationship between Heat Treatment Temperature and Transistor Characteristics (Compound A + Spin Coating)

| | Heat treatment temperature | Mobility (cm$^2$/Vs) | Threshold voltage (V) | ON/OFF ratio |
|---|---|---|---|---|
| Example 3 | Untreated | $2.4 \times 10^{-2}$ | 56 | $10^5$ |
| Ekample 9 | 100° C. | $3.6 \times 10^{-1}$ | 1.3 | $10^5$ |
| Example 10 | 120° C. | $3.7 \times 10^{-1}$ | 0.9 | $10^5$ |
| Example 11 | 140° C. | $4.3 \times 10^{-1}$ | 2.6 | $10^5$ |
| Example 12 | 160° C. | $4.2 \times 10^{-1}$ | 2.4 | $10^5$ |
| Example 13 | 180° C. | $4.0 \times 10^{-1}$ | 1.8 | $10^5$ |

Examples 14 to 17

Fabrication of Organic Thin-Film Transistors with Compound C (PTCDI-C3-O—C2C6)

A silicon substrate, which had on a surface thereof a silicon oxide film (thickness: 200 nm) to be used as agate insulating layer, was provided. An ITO film (150 nm) was formed on the silicon oxide film by sputtering, and using photolithography and wet etching, a pattern of source electrodes and drain electrodes was formed. At that time, the channel length and channel width were 100 μm and 2,000 μm, respectively. Subsequently, the compound C afforded in Synthesis Example 3 was dissolved in chloroform to give a concentration of 1.0%. Using the solution, an organic semiconductor thin film was formed on the silicon substrate by a spin coater (1,500 rpm/60 s). Plural ones of the transistors obtained without heat treatment as described above were then subjected to drying and heat treatment at the predetermined temperatures shown in Table 3, respectively, for 2 hours in a vacuum.

With respect to each transistor obtained as described above, the drain voltage and drain current were measured at different gate voltages. Pronounced saturation regions were observed on drain current-drain voltage curves. It has, therefore, been demonstrated that each transistor is drivable as a field-effect transistor having typical n-type characteristics. The respective heat treatment temperatures and the values of transistor characteristics of the respective transistors as calculated from their $(I_D)^{1/2}$-$V_G$ characteristics are shown in Table 3.

TABLE 3

Relationship between Heat Treatment Temperature and Transistor Characteristics (Compound C + Spin Coating)

| | Heat treatment temperature | Mobility (cm$^2$/Vs) | Threshold voltage (V) | ON/OFF ratio |
|---|---|---|---|---|
| Example 14 | 100° C. | $2.4 \times 10^{-4}$ | 50 | $10^5$ |
| Example 15 | 120° C. | $7.2 \times 10^{-3}$ | 41 | $10^5$ |
| Example 16 | 140° C. | $7.1 \times 10^{-3}$ | 29 | $10^5$ |
| Example 17 | 160° C. | $7.0 \times 10^{-3}$ | 44 | $10^5$ |

Example 18

Fabrication of Organic Thin-Film Transistors with Compound D (PTCDI-C3-O—C4, C12)

A silicon substrate, which had on a surface thereof a silicon oxide film (thickness: 200 nm) to be used as a gate insulating layer, was provided. An ITO film (150 nm) was formed by sputtering, and using photolithography and wet etching, a pattern of source electrodes and drain electrodes was formed. At that time, the channel length and channel width were 100 μm and 1,500 μm, respectively. Subsequently, the compound D afforded in Synthesis Example 4 was dissolved in chloroform to give a concentration of 2.0%. Using the solution, an organic semiconductor thin film was formed on the silicon substrate by a spin coater (1,500 rpm/40 s), followed by drying for 1 hour under reduced pressure in a vacuum.

With respect to the transistors obtained as described above, their transistor characteristics were measured as in the case of Example 1. As a result, it has been demonstrated that these transistors are drivable as field-effect transistors having typical n-type characteristics. The transistor characteristic value, threshold voltage value and ON/OFF ratio calculated from their $(I_D)^{1/2}$-$V_G$ characteristics were $1.3 \times 10^{-3}$ cm$^2$/Vs, 62 V and $10^5$, respectively. The results are shown in Table 4.

Examples 19 to 24

Fabrication of Organic Thin-Film Transistors with Mixture E (PTCDI-C3-O—C12,C14)

A silicon substrate, which had on a surface thereof a silicon oxide film (thickness: 200 nm) to be used as a gate insulating layer, was provided. An ITO film (150 nm) was formed on the silicon oxide film by sputtering, and using photolithography and wet etching, a pattern of source electrodes and drain electrodes was formed. At that time, the channel length and channel width were 100 μm and 1,500 μm, respectively. Subsequently, the mixture E afforded in Synthesis Example 4 was dissolved in chloroform to give a concentration of 2.0%. Using the solution, an organic semiconductor thin film was formed on the silicon substrate by a spin coater (1,500 rpm/40 s), followed by drying for 1 hour under reduced pressure in a vacuum.

With respect to some of the transistors obtained as described above, their transistor characteristics were measured as in Example 1. As a result, it has been demonstrated that these transistors are drivable as field-effect transistors having typical n-type characteristics. The transistor characteristic value, threshold voltage value and ON/OFF ratio calculated from their $(I_D)^{1/2}$-$V_G$ characteristics were $8.3 \times 10^{-3}$ cm$^2$/Vs, 60 V and $10^5$, respectively. The results are shown in Table 4. Further, plural ones of the field effect transistors obtained without any heat treatment were subjected to heat treatment in a vacuum at the respective temperatures shown in Table 4. The heat treatment temperatures and the transistor characteristics of the respective transistors are shown in Table 4.

TABLE 4

Relationship between Heat Treatment Temperature and Transistor Characteristics (Compound D or E + Spin Coating)

| | Heat treatment temperature | Mobility (cm$^2$/Vs) | Threshold voltage (V) | ON/OFF ratio |
|---|---|---|---|---|
| Example 18 | Untreated (Compound D) | $1.3 \times 10^{-3}$ | 62 | $10^5$ |
| Example 19 | Untreated (Compound E) | $8.3 \times 10^{-3}$ | 60 | $10^5$ |
| Example 20 | 100° C. | $5.1 \times 10^{-2}$ | 37 | $10^5$ |
| Example 21 | 120° C. | $4.8 \times 10^{-2}$ | 30 | $10^5$ |
| Example 22 | 140° C. | $1.2 \times 10^{-1}$ | 28 | $10^5$ |
| Example 23 | 160° C. | $8.4 \times 10^{-2}$ | 21 | $10^5$ |
| Example 24 | 180° C. | $8.2 \times 10^{-2}$ | 25 | $10^5$ |

Comparative Examples 1 to 4

Fabrication of Organic Thin-Film Transistors with Compound F (PTCDI-C2-C8)

Organic thin-film transistors of Comparative Example 1 were fabricated as in Example 1 except that the compound A was changed to the compound F (a heteroatom-free compound). Some of the thus-obtained organic thin-film transistors were subjected to heat treatment at varied temperatures, respectively, for 2 hours in a vacuum oven. The heat treatment temperatures in Comparative Examples 2 to 4 were set at 100° C., 140° C. and 160° C., respectively. With respect to the respective transistors so obtained, their transistor characteristics were measured as in Example 1. As a result, they were smaller in both the values of mobility and ON/OFF ratio compared with the corresponding values of the examples. The respective heat treatment temperatures and the values of transistor characteristics of the respective transistors as calculated from their $(I_D)^{1/2}$-$V_G$ characteristics are shown in Table 5.

TABLE 5

Relationship between Heat Treatment Temperature and Transistor Characteristics (Compound F + Spin Coating)

| | Heat treatment temperature | Mobility (cm$^2$/Vs) | Threshold voltage (V) | ON/OFF ratio |
|---|---|---|---|---|
| Comp. Ex. 1 | Untreated | $1.7 \times 10^{-4}$ | 18 | $10^3$ |
| Comp. Ex. 2 | 100° C. | $1.3 \times 10^{-4}$ | 19 | $10^2$ |
| Comp. Ex. 3 | 140° C. | $1.1 \times 10^{-4}$ | 6.3 | $10^2$ |
| Comp. Ex. 4 | 160° C. | $2.6 \times 10^{-4}$ | 3.4 | $10^3$ |

EVALUATION RESULTS

The perylene tetracarboxylic diimide derivatives, which are represented by the formula (1) and characterize the present invention, have made it possible to form good organic semiconductor thin films by a vapor-deposition film-forming process or a solution printing process which is a simple process. It has been confirmed that an organic thin-film transistor fabricated with the organic semiconductor thin film according to the present invention exhibits good transistor characteristics and that its electron mobility can be increased by 10 times or greater when subjected to heat treatment around a phase transition temperature into a liquid crystal state.

On the other hand, the organic thin-film transistors of the comparative examples, which were fabricated with the heteroatom-free perylene tetracarboxylic diimide derivative, had small values in both mobility and ON/OFF ratio, and the effects of the heat treatment did not appear at all because no phase transition took place even when heated.

The present invention has been described based on the preferred examples, although the present invention shall not be limited to the examples.

INDUSTRIAL APPLICABILITY

According to the present invention, useful semiconductor materials can be provided. These useful semiconductor materials make it possible to obtain high electron mobility and high ON/OFF ratio, and further, to form organic semiconductor thin films by a convenient solution coating process that uses the semiconductor materials as solutions. In addition, the present invention can also provide useful organic thin-film transistors of excellent characteristics, which can be fabricated using the organic semiconductor materials.

LEGEND

11 Insulating layer
12 Source electrode
13 Drain electrode
14 Gate electrode
15 Organic semiconductor thin film
16 Substrate

The invention claimed is:

1. An organic semiconductor material comprising a perylene tetracarboxylic diimide derivative represented by following formula (1):

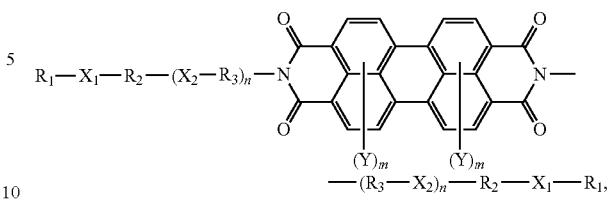

wherein $R_1$ is a linear alkyl group having from 8 to 20 carbon atoms,
$R_2$ is a linear alkyl group having from 2 to 6 carbon atoms,
$R_3$ is a linear alkyl group having from 2 to 6 carbon atoms,
$X_1$ and $X_2$ are each oxygen,
Y is halogen or a cyano group,
m stands for a number from 0 to 4,
n stands for a number from 0 to 2,
wherein the material is soluble in an organic solvent, and
the material forms a thin film having a transistor performance by a printing method or a solution coating method when dissolved in the organic solvent.

2. The organic semiconductor material according to claim 1,
wherein the derivative represented by the formula (1) is an N,N'-bis(3-($R_1$-oxy)-ethyl)-3,4:9,10-perylene tetracarboxylic diimide derivative represented by following formula (2):

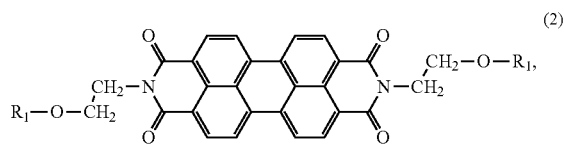

wherein $R_1$ is a linear alkyl group having from 8 to 20 carbon atoms.

3. The organic semiconductor material according to claim 1,
wherein the derivative represented by the formula (1) is an N,N'-bis(3-($R_1$-oxy)-n-propyl)-3,4:9,10-perylene tetracarboxylic diimide derivative represented by following formula (3):

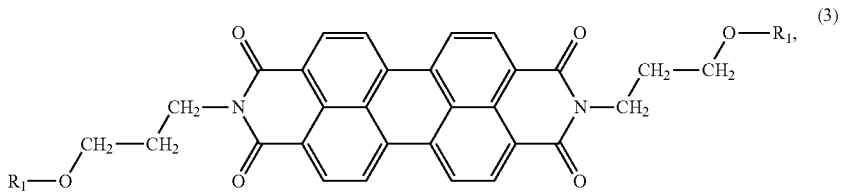

wherein $R_1$ is a linear alkyl group having from 8 to 20 carbon atoms.

4. The organic semiconductor material according to claim 3,
wherein the derivative represented by the formula (3) is N,N'-bis(3-(n-dodecyloxy)-n-propyl)-3,4:9,10-perylene tetracarboxylic diimide represented by following formula (4):

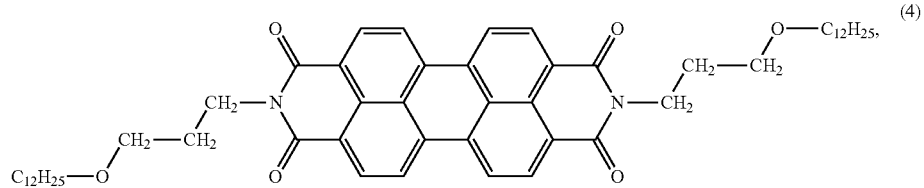

wherein the —$C_{12}H_{25}$ group in the formula (4) is a n-dodecyl group.

5. An organic semiconductor thin film comprising the organic semiconductor material according to claim 1.

6. An organic semiconductor thin film comprising the organic semiconductor material according to claim 1,
wherein the organic semiconductor material has a temperature of a phase transition into a liquid crystal state in a range from 100° C. to 250° C.

7. An organic thin-film transistor; which is formed on a substrate and comprises: a gate electrode; a gate insulating layer; an organic semiconductor thin film; a source electrode; and a drain electrode,
wherein the organic semiconductor thin film comprises the organic semiconductor thin film according to claim 5.

8. An organic thin-film transistor, which is formed on a substrate and comprises: a gate electrode; a gate insulating layer; an organic semiconductor thin film; a source electrode; and a drain electrode,
wherein the organic semiconductor thin film comprises the organic semiconductor thin film according to claim 6, and
the organic semiconductor thin film is a film having been treated with heat at a temperature between 100° C. and 250° C.

9. The organic thin-film transistor according to claim 7, which has an electron mobility from 0.01 to 5.0 cm$^2$/Vs.

* * * * *